United States Patent [19]
Mack

[11] Patent Number: 5,741,949
[45] Date of Patent: Apr. 21, 1998

[54] CONTINUOUS BROMINATION PROCESS AND PRODUCTS THEREOF

[75] Inventor: Art Mack, Lafayette, Ind.

[73] Assignee: Great Lakes Chemical Corporation, West Lafayette, Ind.

[21] Appl. No.: 629,103

[22] Filed: Apr. 8, 1996

Related U.S. Application Data

[63] Continuation-in-part of Ser. No. 318,076, Oct. 5, 1994, abandoned.

[51] Int. Cl.[6] .......................... C07C 41/22; C07C 22/04; C07C 25/18; C09K 21/08
[52] U.S. Cl. .......................... 568/639; 570/184; 570/192; 570/199; 570/206; 252/609; 524/469
[58] Field of Search .......................... 252/609; 524/469, 524/464, 465, 466, 412; 570/206, 184, 199, 192; 568/639

[56] References Cited

U.S. PATENT DOCUMENTS

| | | | |
|---|---|---|---|
| 3,932,542 | 1/1976 | Gems | 570/206 |
| 4,521,633 | 6/1985 | Pedjac | 568/639 |
| 4,709,100 | 11/1987 | Hermolin et al. | 568/639 |
| 4,740,629 | 4/1988 | Brackenridge et al. | 568/639 |
| 4,792,644 | 12/1988 | Hironaka et al. | 570/208 |
| 4,849,560 | 7/1989 | Sekizawn et al. | 570/208 |
| 4,914,247 | 4/1990 | Sekizawa et al. | 570/208 |
| 4,929,785 | 5/1990 | Hussain | 585/426 |
| 4,981,890 | 1/1991 | Schleifstein | 524/169 |
| 4,990,626 | 2/1991 | Hutchinson et al. | 548/462 |
| 4,990,704 | 2/1991 | Stahly | 570/195 |
| 4,997,953 | 3/1991 | McKenna | 548/461 |
| 5,000,879 | 3/1991 | Moore, Jr. et al. | 252/604 |
| 5,003,116 | 3/1991 | Stahly | 570/194 |
| 5,003,117 | 3/1991 | Hussain | 570/210 |
| 5,004,847 | 4/1991 | Beaver et al. | 570/186 |
| 5,004,848 | 4/1991 | Beaver | 570/206 |
| 5,008,417 | 4/1991 | Stahly | 556/104 |
| 5,008,477 | 4/1991 | Hussain | 570/208 |
| 5,017,728 | 5/1991 | McKinnie et al. | 568/726 |
| 5,025,050 | 6/1991 | Torres | 524/91 |
| 5,025,110 | 6/1991 | Beaver | 570/206 |
| 5,030,778 | 7/1991 | Ransford | 570/208 |
| 5,039,729 | 8/1991 | Brackenridge et al. | 524/412 |
| 5,055,235 | 10/1991 | Brackenridge et al. | 252/609 |
| 5,136,107 | 8/1992 | Stephens et al. | 568/639 |
| 5,210,321 | 5/1993 | McKinnie et al. | 568/639 |
| 5,302,768 | 4/1994 | Hussain | 570/185 |
| 5,457,248 | 10/1995 | Mack et al. | 570/206 |

FOREIGN PATENT DOCUMENTS

0571859A2  12/1993  European Pat. Off. ........ C07C 25/18

*Primary Examiner*—Joseph D. Anthony
*Attorney, Agent, or Firm*—Woodard, Emhardt, Naughton, Moriarty & McNett

[57] ABSTRACT

A preferred process for producing a brominated, non-fused aromatic composition involves a continuous bromination in a continuous, mixed reactor such as a continuous stirred tank reactor. Bromine and the aromatic substrate, and optionally a bromination catalyst, are continuously fed to a reaction zone to form a reaction mixture, and the reaction mixture is continuously withdrawn from the reaction zone after an established average residence time. Bromination levels can be readily controlled by controlling the average residence time of the reaction mixture within the reaction zone. Preferred continuos processes also provide mixed, brominated compositions having product distributions which are substantially broader than that obtained by batch brominations conducted to achieve the same level of bromination. Preferred products thus have broad melting ranges which are advantageous in compounding operations.

18 Claims, 1 Drawing Sheet

Product Distribution Continuous Bromination

CONTINUOUS BROMINATION PROCESS AND PRODUCTS THEREOF

REFERENCE TO RELATED APPLICATION

This is a continuation-in-part of U.S. patent application Ser. No. 08/318,076 filed Oct. 5, 1994, now abandoned, which is hereby incorporated herein by reference in its entirety.

BACKGROUND OF THE INVENTION

The present invention generally relates to bromination processes. More particularly, the invention relates to processes for brominating substrates such as non-fused aromatic compounds, to form brominated materials which are useful as flame retardants.

Brominated compositions are commonly compounded into flammable materials such as polymers to serve as flame retardants. Such compounding operations are heavily dependent upon the physical properties of the flame retardant, and thus flame retardants with improper physical properties can be more difficult to effectively compound and confer poor properties to the resulting flame retarded formulation.

Brominated compositions which contain a mixture of brominated homologs and melt over broad temperature ranges are advantageous in compounding operations. Previously, mixed, brominated compositions of diphenyloxide, or DPO, have been prepared in batch reactions. In such reactions, solvents have been used, and the level of bromination has been controlled by controlling the amount of bromine added to the reaction mixture. In the case of brominations without solvent, DPO has been an effective substrate since it and its brominated analogs melt at temperatures sufficiently low to maintain a stirrable reaction mass while achieving the desired level of bromination. However, other non-fused aromatic compounds, for example diphenylalkanes, and their brominated analogs, melt at substantially higher temperatures. Consequently, brominations are complicated because the reaction mixtures must be driven to relatively high temperatures to maintain a workable mixture. Such high temperatures are generally deleterious to the formed product and lead to high color. As a result, batch brominations employing solvents have generally been proposed, e.g. in U.S. Pat. Nos. 5,055,235 and 5,041,687.

In light of the above-noted difficulties, a need exists for bromination processes which can be used to conveniently and reliably achieve products having desired levels of bromination for a broad range of non-fused aromatic substrates. Desirably, the bromination processes would provide mixed, brominated compositions which differ substantially in product distribution and have broader melting ranges than products of corresponding batch bromination processes. The present invention is addressed to these needs.

SUMMARY OF THE INVENTION

Briefly describing one preferred aspect of the invention, provided is a continuous bromination process that produces brominated aromatics at high rates and reactor efficiencies while maintaining low temperatures which can be essential to maintain a quality product. The bromination is typically conducted in a continuous stirred tank reactor (CSTR) or functionally similar continuous reactor to which bromine and the substrate, and optionally a bromination catalyst, are fed in a continuous fashion while the reacted reaction mass is continuously removed from the reactor. In a preferred process, the reacted reaction mass is then fed to a subsequent continuous contacter, e.g. a CSTR, containing heated water to distill off excess bromine and leave a reaction mass that can be pumped to a filter for isolation of the brominated product.

Accordingly, one preferred embodiment of the invention provides a process for preparing a brominated, non-fused polyaromatic composition. The process comprises continuously feeding liquid bromine and a non-fused aromatic compound to be brominated to a reaction zone to form a reaction mixture. The reaction mixture is maintained in the reaction zone at a temperature at which bromination of the non-fused polyaromatic compound in the presence of the liquid bromine occurs. The reaction mixture is continuously passed through and continuously removed from the reaction zone. The bromination is terminated, for example by quenching with water. By the processing steps, an average residence time for the reaction mixture in the reaction zone is established to provide a brominated, non-fused polyaromatic composition having the desired level of bromination.

Surprisingly, continuous brominations of the invention provide very broad product distributions not provided by batch reactions. Such broad product distributions result in unique, advantageous brominated aromatic flame retardants having broad melting ranges which facilitate compounding operations. As such, additional preferred embodiments of the invention provide flame retardant compositions which can be produced by continuous bromination processes of the invention. One such preferred composition is a brominated diphenylalkane composition comprised 40–60 weight percent of hexabromodiphenylalkane, 25–35 weight percent of heptabromodiphenylalkane and 25–35 weight percent of octabromodiphenylalkane, particularly in which the weight percent of hexabromodiphenylethane is less than the sum of the weight percents of heptabromodiphenylalkane and octabromodiphenylalkane, thus ensuring a relatively broad distribution and advantageous melting ranges.

Another preferred composition is a diphenylalkane flame retardant comprised 20–35 weight percent of hexabromodiphenylalkane, 20–35 weight percent of heptabromodiphenylalkane and 20–35 weight percent of octabromodiphenylalkane.

Another such preferred composition is a brominated diphenylalkane composition which is comprised 5–15 weight percent hexabromodiphenylalkane, 7–20 weight percent of heptabromodiphenylalkane, 20–30 weight percent of octabromodiphenylalkane, 25–40 weight percent of non-abromodiphenylalkane and 10–25 weight percent of decabromodiphenylalkane.

Still another such preferred composition is a brominated diphenylalkane product comprised 7–15 weight percent of octabromodiphenylalkane, 30–45 weight percent of non-abromodiphenylalkane and 30–45 weight percent of decabromodiphenylalkane.

The invention thus provides continuous bromination processes which can be used to achieve brominated products having advantageous, broad product distributions and broad melting ranges. The preferred brominated products of the invention are useful as flame retardants for flammable macromolecular materials and demonstrate excellent properties in compounding operations.

Additional preferred embodiments, features and advantages of the invention will be apparent from the following description.

DESCRIPTION

Figure 1:
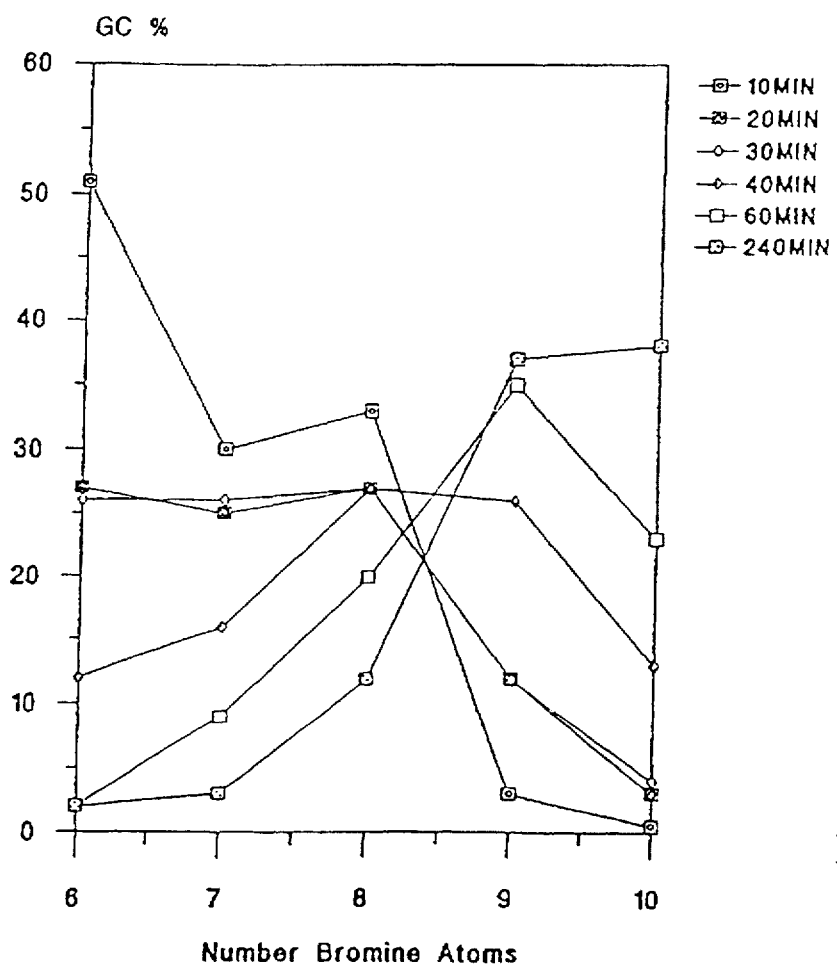
FIG. 1 is a graph illustrating the bromination levels achieved by varying the average substrate residence time in a continuous bromination reactor, as described in the Examples.

For the purpose of promoting an understanding of the principles of the invention, reference will now be made to certain preferred embodiments thereof and specific language will be used to describe the same. It will nevertheless be understood that no limitation of the scope of the invention is thereby intended, such alterations, further modifications and applications of the principles of the invention as described herein being contemplated as would normally occur to one skilled in the art to which the invention relates.

Preferred preparative processes of the invention involve the bromination of a non-fused aromatic substrate using bromine as the brominating agent. In this regard, the bromine employed in the bromination process can be but is not necessarily purified to remove organic impurities such as grease, oil and carbonyl-containing hydrocarbons, by means such as distillation or treatment with a concentrated mineral acid such as sulfuric acid. These and other modes of purifying bromine are well known to the ordinarily skilled artisan. Bromine of high purity is also available from commercial sources.

The amount of bromine used will depend upon several factors including whether any other solvents are present. In preferred brominations with bromine as the sole solvent, a stoichiometric excess of bromine of at least about 100% is employed (i.e. at least double the amount of bromine which is stoichiometrically required to achieve the desired level of ar-bromination is employed).

The preferred substrates employed in the bromination procedure can be completely unbrominated, or can be partially brominated albeit to an extent less than that desired. Illustrative preferred substrates for bromination include those of the general formula:

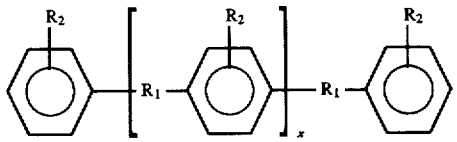

wherein $R_1$ is a direct bond, an alkylene radical having up to about 10 carbon atoms, O, CO, S, or $SO_2$; $R_2$ is H, OH or $NH_2$; and x is an integer from zero up to about 2000. Illustrative substrates include a wide variety of known non-fused polyaromatic compounds, including for instance biphenol, bisphenol-A, trimethylphenyl indan, diphenoxyethane, as well as oligomers and polymers (e.g. novolak or phenol-formaldehyde condensates, polystyrene, and the like).

More preferred substrates will be encompassed by the formula:

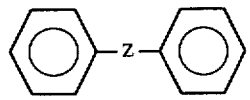

wherein z is an organic or inorganic divalent radical providing thermal stability to the molecule, for example an oxygen atom (O) or an alkylene radical having from 1 to about 10 carbon atoms. Thus, suitable more preferred substrates include diphenyloxide, diphenylmethane, 1,2-diphenylethane, 1,3-diphenylpropane, 1,4-diphenylbutane, 1,5-diphenylpentane, 1,6-diphenylhexane, 1,7-diphenylheptane, 1,8-diphenyloctane, 1,9-diphenylnonane, and 1,10-diphenyldecane. 1,2-diphenylethane (referred to herein sometimes simply as "diphenylethane") is a particularly preferred diphenylalkane reactant. Like the bromine employed, the diphenylalkane substrate can be but is not necessarily highly purified.

Brominations of the invention can be achieved with or without the use of a bromination catalyst. When used, the bromination catalyst will have sufficient catalytic activity to provide the level of bromination desired. Suitable bromination catalysts include aluminum catalysts such as aluminum powder and aluminum trihalides (e.g. $AlCl_3$ or $AlBr_3$), iron catalysts such as iron powder or iron trihalides (e.g. $FeCl_3$ or $FeBr_3$), antimony, zirconium, and the like. The bromination catalyst will be used in a catalytic amount. Usually about 0.1 to about 20 weight percent of catalyst is used relative to the weight of the non-fused aromatic substrate, and more typically this value is about 1 to 10 percent.

When brominating a diphenylalkane substrate, it is preferred to employ a catalyst and/or reaction conditions which do not lead to substantial bromination of the alkane portion of the molecule. Iron catalysts such as iron and iron salts, e.g. iron trihalides, are particularly advantageous catalysts for these purposes.

Generally, processes of the invention will employ a continuous, mixed reactor setup, in which reactants are continuously charged to and product is continuously removed from the reactor. In preferred processes, at least two feed ports and one product removal port will be provided for the reactor. The non-fused aromatic substrate to be brominated, in solid particulate or molten form, and/or dissolved in a suitable solvent such as a halogenated lower alkane, e.g. methylene dibromide, methylene dichloride, chloroform, bromoform, or the like, is fed to the reactor via one or more reactor feed ports. In this regard, the substrate to be brominated can be fed above or below the surface of the reaction mixture in the reactor. In the latter mode, a dip tube, as is commonly employed in feeding reactants subsurface, can be utilized. When an oxidation-sensitive substrate, such as a diphenylalkane, is employed, it can be maintained under an inert atmosphere such as a nitrogen blanket prior to feed to the reactor, particularly when fed in the molten state.

In preferred reactions, bromine will also be continuously fed to the reactor via a reactor feed port. As indicated above, the bromine employed in the bromination process can be but is not necessarily purified to remove organic impurities such as grease, oil and carbonyl-containing hydrocarbons.

The catalyst, when used, can be provided via its own, separate port to the continuous reactor, or can be provided dissolved in the bromine feed. When separately fed to the reactor, the catalyst can be dissolved in a suitable solvent, including for example additional bromine or a halogenated lower alkane (i.e. $C_1$ to $C_5$ alkane) such as methylene dibromide or dichloride, bromoform, chloroform, and the like.

During the feed of the non-fused aromatic substrate, the bromine, and any catalyst, it is preferred that the reaction mixture to which these materials are fed be maintained at a relatively low temperature, preferably in the range of about 0° C. to about 40° C., more preferably in the range of about 0° C. to about 30° C. After the addition of the diphenylalkane reactant is complete, the bromination reaction can be conducted at any temperatures suitable to provide the desired product. The reaction temperature or temperatures can be maintained with or without the external application of heat or cooling, with reaction temperatures in the range of about 20° C. up to about 60° C. being typical.

Moreover, two or more continuous reactors, connected in series, can be dedicated to the bromination phase of the process. These reactors can be operated at the same or at different temperatures. It can be advantageous to operate the first of a plurality of continuous bromination reactors connected in series at relatively lower temperatures, and latter reactors at higher temperatures. Such an arrangement allows the reactants to be combined at the desired, relatively low temperatures during the early stages of the bromination in order to avoid product discoloration, and the reaction temperature to be higher at later stages of the bromination in order to speed the reaction rate and achieve higher levels of bromination more quickly. For example, desirable processes can be conducted wherein a first bromination-dedicated continuous reactor is operated at a temperature in the range of 0° C. to 40° C., for example 0° C. to 20° C. when cooling is applied or 20° C. to 40° C. with no cooling applied. One or more subsequent bromination-dedicated continuous reactors can then operated at a temperature or temperatures in the range of about 40° C. to 60° C., and more typically in the range of about 50° C. to about 60° C. when higher levels of bromination are desired.

Preferred inventive processes will employ excess bromine as the solvent. Such processes provide higher reaction rates than corresponding reactions employing substantial amounts of other solvents, while allowing for easy isolation via steam stripping to leave the brominated product as a slurry in water.

Preferred bromination reactions are conducted for a sufficient duration to achieve a brominated diphenyloxide or diphenylalkane product having an average bromine number of about 6 to 10, that is, having about 6 to 10 aromatically-bound bromines, or ar-bromines, per molecule.

Preferred such brominated products will have the formula:

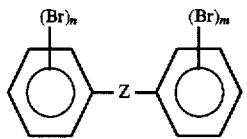

wherein Z is —O— or an alkylene radical having 1 to about 10 carbon atoms, n and m are each a number from 1 to 5, and n+m, on average, is in the range of about 6 to about 10.

The duration selected for the bromination reaction, as determined by the average residence time of the reaction mixture in the bromination-dedicated continuous reaction zone(s), will be dependent upon several factors such as the extent of bromination desired, the particular temperature and catalyst employed and the scale of the reaction. Typical average residence times within the one or more bromination zones will be about 1 minute or more, for example in the range of about 1 minute to about 24 hours.

The brominated diphenylalkane product can be isolated from the reaction mixture in any conventional manner. Preferably, the product is isolated by contacting the reaction mixture with hot water to quench the bromination and distill off any excess bromine. For example, this may be accomplished by pumping the reacted mixture from a bromination-dedicated continuous reactor into another vessel containing hot water to distill off any remaining bromine and leave the product in an aqueous slurry. The recovered bromine can then optionally be recycled to the bromine feed at the start of the process. To facilitate the transfer of the reaction mixture among continuous reactors or other vessels, it is preferred to use a stoichiometric excess of bromine that will provide a pumpable medium during and upon completion of the reaction. A metal chelating or complexing agent can be included in the hot water to aid in the removal of catalyst residues. Suitable chelating or complexing agents include for example sodium gluconate, glycolic acid, EDTA and similar bidentate ligands.

The brominated diphenylalkane product can be recovered from the aqueous slurry by filtration and can be washed further with water or with organic solvents such as alcohols, e.g. isopropyl alcohol, ketones, e.g. acetone, aromatics, e.g. toluene, halogenated lower alkanes, e.g. methylene dichloride, methylene dibromide, chloroform, bromoform and the like, to remove impurities from the product.

Brominated diphenylalkane products, especially those having alkylene-bridge-bromination (e.g. resulting from a bromination using an aluminum or aluminum trihalide catalyst), can be digested with a substance that is effective to react off or otherwise remove the aliphatically-attached bromines. For example, the product can be digested in a treatment solution containing a halogen reducing agent, e.g. an aqueous basic solution containing ammonia, hydrazine, organic amines and the like.

If desired, to improve the color and other properties of the product, the product can be subjected to a high temperature solvent treatment. The solvent used in the high temperature treatment of the present invention must not decompose at the temperatures at which at least a substantial portion (e.g. 10% or more) of the brominated composition dissolves in the solvent. These temperatures will vary in accordance with the particular brominated substrate and the level of bromination of the products, with lower brominated products typically dissolving at lower temperatures than higher brominated materials. Temperatures in the range of about 80° C. to about 300° C. will be typical.

To perform the high temperature solvent treatment, the brominated diphenylalkane is contacted with the solvent at a temperature sufficiently high that the brominated diphenylalkane is at least partially dissolved in the solvent. The brominated composition is preferably slurried in the solvent at a temperature below that which is necessary to substantially dissolve the brominated composition, and the slurry is heated to a temperature sufficiently high to dissolve at least a portion of the composition.

Some preferred aromatic solvent materials useful for these purposes include alkylated benzenes such as toluene and xylenes, as well as non-fused polyaromatic compounds such as biphenyls, diphenylalkanes (e.g. with $C_1$ to $C_{10}$ alkylene bridges), diphenyloxides diphenylsulfones, diphenylcarbonate, and the like, which are thermally stable at the treatment temperatures employed. Mixtures of these materials are also suitable, such as may be found in certain Dowtherm heat transfer agents available from Dow Chemicals of Midland, Mich., for example Dowtherm A (a utectic mixture of biphenyl and diphenyloxide). Other Dowtherm products such as Dowtherm G (biphenyl phenyl ether) may also be used. Non-aromatic solvents, for example alcohols such as isopropanol, can also be used in heated solvent treatments to treat and improve the inventive products.

After dissolution of at least a portion of the brominated composition, the resulting mixture is caused to be at a temperature at which the dissolved composition precipitates. In this regard, the solution can be actively cooled to reduce temperature or may simply be allowed to cool on its own. It is preferable to apply cooling to the solution (as can be achieved in a heating/cooling jacketed vessel), as this results in smaller particle size upon precipitation of the brominated material. Additionally, a non-solvent can be added to facilitate precipitation of the dissolved product from the mixture.

After recovery and any ensuing solvent treatments, the solid brominated product can be dried, usually at a temperature above about 100° C. After drying, the solid brominated product can be roasted or oven-aged at temperatures above about 200° C.

The brominated product is also preferably treated to reduce its particle size. For instance, the product can be mechanically ground or micronized, such as by air milling, including hot air milling, or similar known procedures. The reduction in particle size can be carried out before, during and/or after any drying or roasting procedure.

It is contemplated that products of the present invention will have YID's in the range of about 1 to about 20, with YID's in the range of 1 to about 12 being preferred.

As indicated above, products resulting from the inventive continuous brominations substantially differ from products available from batch-style brominations. Preferred products of the invention, generally speaking, will be mixtures of compounds brominated to various extents, having a broader product distribution than that which is achieved by batch brominations.

Broad product distributions as achieved by the present invention provide broad melting ranges, a highly desired characteristic for flame retardants which facilitates compounding operations. Thus, provided by the invention is a series of unique brominated flame retardants having varying average bromine numbers coupled with advantageous product distributions and melting point ranges.

One such preferred product of the invention is a flame retardant comprising a brominated diphenylalkane composition which is comprised 40–60 weight percent of hexabromodiphenylalkane, 25–35 weight percent of heptabromodiphenylalkane and 25–35 weight percent of octabromodiphenylalkane. Preferred processes of the invention generally result in such products in which the weight percent of hexabromodiphenylethane is less than the sum of the weight percents of heptabromodiphenylalkane and octabromodiphenylalkane, thus ensuring a relatively broad distribution and advantageous melting ranges. Preferred such products are further characterized by having an average bromine number of 6.4 to 6.6, a melting point start in the range of 130°–150° C., and a melting point end in the range of 170°–200° C. More preferably, such products will have a melting point start in the range of 130°–140° C. and a melting point end in the range of 180°–190° C.

The invention also provides a preferred diphenylalkane flame retardant which is comprised 20–35 weight percent of hexabromodiphenylalkane, 20–35 weight percent of heptabromodiphenylalkane and 20–35 weight percent of octabromodiphenylalkane. Preferred such products are further characterized by having an average bromine number of 6.7 to 7.5, a melting point start of 140'–170° C., and a melting point end in the range of 240°–290° C. Even more preferably, such products have a melting point start in the range of 140°–155° C. and a melting point end in the range of 240°–270° C.

Also provided by the invention is a preferred brominated diphenylalkane flame retardant which is comprised 5–15 weight percent of hexabromodiphenylalkane, 7–20 weight percent of heptabromodiphenylalkane, 20–30 weight percent of octabromodiphenylalkane, 25–40 weight percent of nonabromodiphenylalkane and 10–25 weight percent of decabromodiphenylalkane. Such products are also preferably characterized by having an average bromine number in the range of 7.6 to 8.2, a melting point start in the range of 170°–200 ° C., and a melting point end in the range of 270°–320° C. Especially preferred products of this class will begin melting in the range of 170°–180° C., and end melting in the range of 270°–280° C.

The invention further provides a flame retardant having a relatively higher bromine level. Thus, a preferred flame retardant is comprised 7–15 weight percent of octabromodiphenylalkane, 30–45 weight percent of nonabromodiphenylalkane and 30–45 weight percent of decabromodiphenylalkane. More preferably, the flame retardant is comprised 10–15 weight percent of octabromodiphenylalkane, and 30–40 weight percent of each of nonabromodiphenylalkane and decabromodiphenylalkane. Further preferred characteristics of such products include an average bromine number of 8.3 to 8.9, a melting point start in the range of 220°–250° C., and a melting point end in the range of 290°–320° C. Highly advantageous such products will have a melting point start in the range of 220°–230° C. and a melting point end in the range of 290°–320° C.

The brominated flame retardant products of the invention can be conventionally incorporated into flammable materials in flame retardant amounts. Generally, the flammable material will be a macromolecular material such as a polymer. Representative polymers in which products of the present invention may be used include polystyrene, including high impact polystyrene; copolymers of styrene; polycarbonates; polyurethanes; polyimides; polyamides; polyethers; acrylics; polyesters; epoxies; phenolics; elastomers such as butadiene/styrene copolymers and butadiene/acrylonitrile copolymers; terpolymers of acrylonitrile, butadiene and styrene; natural rubber; butyl rubber and polysiloxanes. Additional representative polymers include those of olefinically saturated monomers such as ethylene, propylene and butadiene; copolymers of two or more such alkylene monomers; copolymers of one or more such alkylene monomers, etc. Blends of polymers may also be used.

The amount of brominated flame retardant product necessary for flame retardancy will depend upon the particular brominated substrate employed and polymer material involved, as well as other flame retardants which might be included. Those of ordinary skill in the art will be readily able to incorporate an amount of the flame retardant which is necessary to achieve the desired level of flame retardancy. As is well known, it is preferred to incorporate the brominated flame retardant with another flame retardant material such as an inorganic compound, e.g. ferric oxide, zinc oxide, zinc borate, a group V element oxide such as a bismuth, arsenic, phosphorus or an antimony oxide. Of these, antimony oxide has long been used on the commercial scale and thus it is a preferred additional flame retardant. When an inorganic flame retardant is used in combination with the brominated flame retardant, the inorganic compound and brominated flame retardant will usually be present in a ratio of about 1:1 to about 1:10, more usually in the range of about 1:2 to about 1:4.

Generally speaking, polymer formulations contain up to about 40 wt % of the flame retardant system, whether it be the brominated flame retardant alone or its combination with another flame retardant. More typically, this range is about 10 to 30 wt %

Polymer formulations incorporating flame retardants of the invention can be conventionally processed to form thermoplastic articles, for example by molding (e.g. injection, extrusion or compression molding). Depending on the particular application, the polymer formulation will contain further conventional additives such as pigments, fillers, UV stabilizers, plasticizers, antioxidants, and the like.

In order to promote a further appreciation and understanding of the present invention, the following specific Examples are provided. It will be understood that these examples are illustrative and not limiting in nature. In these Examples, the following abbreviations are used: g=grams; ml=milliliters; hexa Br=hexabromodiphenylethane; hepta Br=heptabromodiphenylethane; octa Br=octabromodiphenylethane; nona Br=nonabromodiphenylethane; deca Br=decabromodiphenylethane. The melting points discussed herein were determined with a heating rate of 1° C. per minute. In the Examples, a Buchi 510 capillary melting point apparatus was used for this purpose. The initial melting point was recorded when the material began to shrink from the walls of the capillary, and the final melting point was recorded when a meniscus formed in the capillary.

EXAMPLE 1

Batch Bromination of DPE in Bromine
(Comparative)

Diphenylethane (DPE) (36.5 g, 0.2 moles) was melted and added to bromine (639.2 g, 4.0 moles containing 1.45 g of dissolved iron) over 16 minutes with stirring while maintaining the temperature at 0° to −5° C. using a cooling bath. After all the DPE was added the cooling bath was removed and the reaction mixture was stirred for a further 14 minutes (total bromination time of 30 minutes) by which time the temperature was 31° C. Water (1,000 g with 11.3 g of Na gluconate dissolved) was added to quench the bromination and the reaction mixture heated to remove the bromine and leave the resulting solid as a suspension in water. The solid was filtered and washed with water until the filtrate was pH of 6 and negative to dissolved iron (potassium thiocyanate). The crude product was analyzed by gas liquid chromatography (glc) to ascertain the brominated species present and the melting point (Mpt) range. The results of an initial run and a repeat run are set forth in Table 1 below.

TABLE 1

| Penta Br | Hexa Br | Hepta Br | Octa Br | Nona Br | Deca Br | Mpt Range |
|---|---|---|---|---|---|---|
| 0% | 57% | 23% | 12% | 4% | 4% | 155–184° C. |
| 1% | 77% | 15% | 2% | 0.2% | 0.7% | 157–200° C. |

EXAMPLE 2

A 500 ml 3-necked flask was equipped with a pressure equalized bottom drain, heated dropping funnel, bromine inlet tube, stirrer and condenser with gas take off going to an HBr scrubber. Flexible Viton tubing was attached to the bottom drain valve and this was passed through a Masterflex reversible pump to a stripper vessel which consisted of a heated 3-liter beaker equipped with a stirrer, Dean & Stark trap and a condenser equipped with HBr scrubber. Iron powder was predissolved in bromine and used as a feed for the reactor via the bromine inlet tube. DPE was melted and added to the heated dropping funnel in preparation for addition. Bromine was pumped into the reactor (200 ml) and DPE added (25 ml in 30 min). The bottom drain valve was then opened and the reaction mixture pumped to the stripper vessel at 6 ml per minute, the stripper vessel containing heated water to strip the bromine (which can be dried and recycled). Sodium gluconate was also included in the water strip as a chelating agent for the iron catalyst. The reaction level in the reaction vessel was maintained at 200 ml by adding fresh DPE and bromine (with dissolved catalyst). The material collected for the first hour was discarded (not representative of steady sate). After one hour the material was pumped (6 ml per minute, i.e. 30 minutes residence time for 200 ml volume) to the stripper vessel, and the product was then collected for analysis. The bromination temperature was 25° C. throughout the run. The product, slurried in water, was pumped from the stripper vessel and isolated and analyzed as in Example one. The results are set forth in Table 2 below.

TABLE 2

| Penta Br | Hexa Br | Hepta Br | Octa Br | Nona Br | Deca Br | Mpt Range |
|---|---|---|---|---|---|---|
| 0% | 26% | 26% | 27% | 12% | 4% | 148–257° C. |

EXAMPLES 3–8

Continuous brominations were carried out as in Example 2 but the residence time (RT) was decreased and increased by altering pumping rates and volume in the CSTR. The results are summarized in Table 3 below and FIG. 2, illustrating that a broad range of distributions are achievable in accordance with the invention.

TABLE 3

| RT | Penta Br | Hexa Br | Hepta Br | Octa Br | Nona Br | Deca Br | Mpt Range |
|---|---|---|---|---|---|---|---|
| 10 min Ex. 3 | 0% | 51% | 30% | 33% | 3% | 0.5% | 135–183° C. |
| 20 min Ex. 4 | 0% | 27% | 25% | 27% | 12% | 3% | 151–235° C. |
| 30 min Ex. 5 | 0% | 26% | 26% | 27% | 12% | 4% | 148–257° C. |
| 40 min Ex. 6 | 0% | 12% | 16% | 27% | 26% | 13% | 166–283° C. |
| 60 min Ex. 7 | 0% | 6% | 9% | 20% | 35% | 23% | 198–300° C. |
| 4 hr Ex. 8 | 0% | 2% | 3% | 12% | 37% | 38% | 236–319° C. |

EXAMPLE 9

Crude reaction mixture from Example 6 (100 g) was charged to a reactor equipped with a stirrer, thermometer and Dean & Stark apparatus. Toluene (200 ml) was added and the mixture was brought up to reflux, and residual water from the wet cake was collected in the Dean & Stark. After refluxing for one hour (not all material was in solution) the mixture was cooled to below 70° C. and methanol added dropwise (300 ml), this caused further precipitation of product. The product was cooled to 25° C. and filtered, washed with methanol (2×300 ml) and dried in an oven at 100° C. for 3 hours. The final product (95% recovery from crude) was characterized as set forth in Table 4.

TABLE 4

| Sample | % OBr | Hydrolyzeable Bromine | Residual Bromide | Mpt Range | Hexa Br | Hepta Br | Octa Br | Nona Br | Deca Br |
| --- | --- | --- | --- | --- | --- | --- | --- | --- | --- |
| Crude | 78.3 | 3400 ppm | 1195 ppm | 166–283° C. | 12% | 16% | 27% | 26% | 13% |
| Purified | 79.4 | 1700 ppm | 80 ppm | 178–278° C. | 11% | 14% | 27% | 27% | 14% |

EXAMPLE 10 (COMPARATIVE)

DPE (182.27 g , 1 mole) and iron powder (0.91 g) were charged to a 1 liter flask that was equipped with a nitrogen purge, stirrer, HBr scrubber and heating mantle. The system was purged with nitrogen and heat applied to melt the DPE (60° C.). Bromine (1329.8 g) was then added dropwise to the reactor (HBr was liberated and trapped) over 16 hours. The temperature was raised as bromine addition progressed in order to keep the contents of the reactor liquid and stirreable, the final temperature reached was 193° C. The reaction mixture was then allowed to cool and at 107° C. toluene (600 ml) was added and allowed to cool to room temperature overnight. Sodium carbonate powder (19.71 g) w added to the reactor and heat applied (ppt iron carbonate formed). Refluxed for 3 hours (dark brown solution) and then filtered through a sinter, a tan color solid was removed. The toluene was removed by stripping under vacuum to leave a dark red-black glassy solid. After grinding on a mortar and pestle the resulting powder had a YID of 99. The organic bromine content was 68.78% and hydrolyeazable bromine was 7622 ppm.

EXAMPLE 11

A brominated diphenylethane product was compounded into ABS at a load level which gave V-0 flammability performance and tested for color stability according to the ASTM D 4459 for indoor applications. The brominated product was a mixture of hexabromo-, heptabromo-, octabromo-, nonabromo-, and decabromodiphenylethane from a process such as that in Example 8 above. Excellent compounding properties were exhibited by the flame retardant product. The resulting thermoplastic composition exhibited the characteristics set forth in Table 5 below (944 FL=Chimaasorb 944L; Delta E=UV Stability, 300 hrs, ASTM D4459).

TABLE 5

| % Br | % FR | % ATO | Tinuvin 327 | 944 FL | UL94, 1/16" | Delta E |
| --- | --- | --- | --- | --- | --- | --- |
| 10.4% | 13.7% | 3.2% | 0.5% | 0.5% | V-0 | 6.5 |

While the invention has been described in some detail in the foregoing passages, it will be understood that the discussions herein are illustrative of the invention and that alterations, modifications or additions can be made to the described procedures without departing from the spirit and scope of the applicant's invention.

What is claimed is:

1. A process for preparing a brominated, non-fused aromatic composition, comprising:
   a) continuously feeding liquid bromine and a non-fused aromatic compound to be brominated to a reaction zone to form a reaction mixture, said reaction zone including an input and an output at spaced locations, and said liquid bromine being fed to the reaction zone in at least about a 100% stoichiometric excess relative to that necessary to produce said brominated, non-fused aromatic composition;
   b) maintaining the reaction mixture in the reaction zone at a temperature at which bromination of the non-fused polyaromatic compound in the presence of the liquid bromine occurs;
   c) continuously passing the reaction mixture through the reaction zone from the input of the reaction zone to the output of the reaction zone;
   d) continuously withdrawing the reaction mixture from the output of the reaction zone; and
   e) terminating the bromination of the non-fused aromatic compound;

wherein an average residence time for the reaction mixture in the reaction zone is established to provide the brominated, non-fused aromatic composition.

2. The process of claim 1 also comprising continuously feeding a bromination catalyst to the reaction zone to form a component of the reaction mixture.

3. The process of claim 1 wherein the aromatic compound is encompassed by the formula:

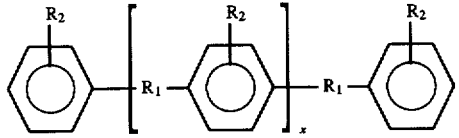

wherein $R_1$ is a direct bond, an alkylene radical having up to about 10 carbon atoms, O, CO, S, or $SO_2$; $R_2$ is H, OH or $NH_2$; and x is an integer from zero up to about 2000.

4. The process of claim 3 wherein the aromatic compound is encompassed by the formula:

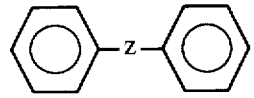

wherein Z is O or an alkylene radical having up to about 10 carbon atoms.

5. The process of claim 3 wherein the non-fused aromatic compound is diphenyloxide.

6. The process of claim 3 wherein Z is an alkylene radical having up to about 10 carbon atoms.

7. The process of claim 6 wherein the non-fused aromatic compound is diphenylethane.

8. The process of claim 3 also comprising continuously feeding a bromination catalyst to the reaction zone to form a component of the reaction mixture.

9. The process of claim 8 wherein the reaction mixture to which the bromine, non-fused aromatic compound and catalyst are fed is at a temperature of about 0° C. to about 40° C.

10. The process of claim 9 wherein the non-fused aromatic compound is diphenylethane.

11. A process for preparing a brominated diphenyloxide or diphenylalkane composition having about 6 to about 10 ar-bromines per molecule, comprising:

continuously feeding to a reaction zone, liquid bromine and a compound of the formula

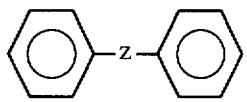

wherein Z is O or an alkylene radical having from 1 to about 10 carbon atoms, to form a reaction mixture, said liquid bromine being fed to said reaction zone in at least about a 100% stoichiometric excess relative to that necessary to produce said brominated diphenyloxide or diphenylalkane composition;

maintaining the reaction mixture in the reaction zone at a temperature at which bromination of said compound in the presence of liquid bromine occurs; and continuously withdrawing the reaction mixture from the reaction zone;

wherein an average residence time for the reaction mixture in the reaction zone is established to provide the brominated diphenyloxide or diphenylalkane composition having an average of about 6 to about 10 ar-bromines per molecule.

12. The process of claim 11, wherein Z is O.

13. The process of claim 11, wherein Z is an alkylene radical having from 1 to about 10 carbon atoms.

14. The process of claim 13, wherein said composition is comprised 20-35 weight percent of hexabromodiphenylalkane, 20-35 weight percent of heptabromodiphenylalkane, and 20-35 weight percent of octobromodiphenylalkane.

15. The process of claim 13, wherein said composition is comprised 5-15 weight percent hexabromodiphenylalkane, 7-20 weight percent of heptabromodiphenylalkane, 20-30 weight percent of octobromodiphenylalkane, 25-40 weight percent of nonobromodiphenylalkane, and 10-25 weight percent of decabromodiphenylalkane.

16. The process of claim 13, wherein said composition is comprised 7-15 weight percent of octobromodiphenylalkane, 30-45 weight percent of nonobromodiphenylalkane, and 30-45 weight percent of decabromodiphenylalkane.

17. The process of claim 13, wherein said composition is comprised 40-60 weight percent of hexabromodiphenylalkane, 25-35 weight percent of heptabromodiphenylalkane, and 25-35 weight percent of octobromodiphenylalkane.

18. The process of claim 17, wherein the weight percent of hexabromodiphenylalkane is less then the sum of the weight percents of heptabromodiphenylalkane and octobromodiphenylalkane.

* * * * *